United States Patent [19]

Dietz et al.

[11] Patent Number: 5,653,714
[45] Date of Patent: Aug. 5, 1997

[54] DUAL SLIDE CUTTING GUIDE

[75] Inventors: Terry L. Dietz, Columbia City; Richard D. Vanlaningham, Milford, both of Ind.

[73] Assignee: Zimmer, Inc., Warsaw, Ind.

[21] Appl. No.: 605,403

[22] Filed: Feb. 22, 1996

[51] Int. Cl.$^6$ .................................................. A61F 5/04
[52] U.S. Cl. ............................. 606/87; 606/88; 606/96
[58] Field of Search ................... 606/79, 80, 86, 606/87, 88, 89, 96, 97, 98

[56] References Cited

U.S. PATENT DOCUMENTS

| | | | |
|---|---|---|---|
| 4,457,307 | 7/1984 | Stillwell | 128/317 |
| 4,459,985 | 7/1984 | McKay et al. | 128/303 R |
| 4,467,801 | 8/1984 | Whiteside | 128/303 R |
| 4,487,203 | 12/1984 | Androphy | 128/303 R |
| 4,567,885 | 2/1986 | Androphy | 128/92 H |
| 4,574,794 | 3/1986 | Cooke et al. | 128/92 H |
| 4,703,751 | 11/1987 | Pohl | 606/87 |
| 4,721,104 | 1/1988 | Kaufman et al. | 128/92 VW |
| 4,722,330 | 2/1988 | Russell et al. | 128/92 |
| 4,759,350 | 7/1988 | Dunn et al. | 128/92 |
| 4,787,383 | 11/1988 | Kenna | 128/303 R |
| 4,892,093 | 1/1990 | Zarnowski et al. | 606/82 |
| 4,926,847 | 5/1990 | Luckman | 606/88 |
| 4,952,213 | 8/1990 | Bowman et al. | 606/79 |
| 5,007,912 | 4/1991 | Albrektsson et al. | 606/87 |
| 5,035,699 | 7/1991 | Coates | 606/86 |
| 5,047,032 | 9/1991 | Jellicoe | 606/83 |
| 5,053,037 | 10/1991 | Lackey | 606/79 |
| 5,092,869 | 3/1992 | Waldron | 606/82 |
| 5,098,436 | 3/1992 | Ferrante et al. | 606/88 |
| 5,112,336 | 5/1992 | Krevolin et al. | 606/96 |
| 5,122,144 | 6/1992 | Bert et al. | 606/88 |
| 5,129,907 | 7/1992 | Heldreth et al. | 606/80 |
| 5,129,908 | 7/1992 | Petersen | 606/80 |
| 5,171,244 | 12/1992 | Caspari et al. | 606/88 |
| 5,171,276 | 12/1992 | Caspari et al. | 623/16 |
| 5,176,684 | 1/1993 | Ferrante et al. | 606/86 |
| 5,180,384 | 1/1993 | Mikhail | 606/80 |
| 5,190,547 | 3/1993 | Barber et al. | 606/79 |
| 5,201,768 | 4/1993 | Caspari et al. | 623/20 |
| 5,207,680 | 5/1993 | Dietz et al. | 606/86 |
| 5,207,711 | 5/1993 | Caspari et al. | 623/20 |
| 5,228,459 | 7/1993 | Caspari et al. | 128/898 |
| 5,234,433 | 8/1993 | Bert et al. | 606/88 |
| 5,263,498 | 11/1993 | Caspari et al. | 128/898 |
| 5,304,181 | 4/1994 | Caspari et al. | 606/80 |
| 5,344,423 | 9/1994 | Dietz | 606/87 |
| 5,417,695 | 5/1995 | Axelson, Jr. | 606/89 |
| 5,454,816 | 10/1995 | Ashby | 606/88 |

FOREIGN PATENT DOCUMENTS

| | | | |
|---|---|---|---|
| 0 104 732 | 4/1984 | European Pat. Off. | A61B 17/14 |
| 555003 | 8/1993 | European Pat. Off. | 606/88 |

Primary Examiner—Michael Buiz
Assistant Examiner—David O. Reip
Attorney, Agent, or Firm—Todd A. Dawson

[57] ABSTRACT

The guide of this invention provides an alternative to a system requiring a plurality of guides or for a guide with a plurality of slots by providing a single guide which slides along the distal femur and which articulates to accommodate a variety of angles. The guide includes a base portion defining a pair of parallel rails having a dove-tail shaped groove formed therein. The base is fixed to the distal end of the femur after an initial cut has been made to flatten the distal end. The device further includes an upper frame which is carried by the base and slides along the rails. The upper frame pivotally supports a carriage assembly in a plurality of discrete angles as determined by detents. The carriage includes a pair of parallel rods which extend in a direction transverse to the parallel rails of the base portion. In the preferred embodiment, the parallel rods support a milling guide which is slidable along the rods. The milling guide is configured to accommodate an elongated milling burr extending therethrough for removal of a portion of the patient's bone.

4 Claims, 7 Drawing Sheets

DUAL SLIDE CUTTING GUIDE

FIELD OF THE INVENTION

This invention relates to cutting or milling guides as used in orthopaedic surgery to prepare the patient's bone to accommodate an orthopaedic implant and has specific reference to a guide capable of making a plurality of cuts using a shiftable guide.

BACKGROUND OF THE INVENTION

Heretofore, cutting or milling guides used to guide a saw blade or milling burr along the surface of a bone were typically fixed relative to the bone. When forming the distal femur to accommodate a femoral knee implant, five separate surfaces are formed. Therefore, to form all of the surfaces, a single guide having a plurality of openings or a series of guides is required. Generally, most manufactures have designed a series of guides which connect to a single reference point on the femur for guiding a blade over the surface of the bone. However, systems are available which enable the surgeon to make several cuts with one fixed guide. The guide includes a plurality of saw blade slots to guide a blade and make a plurality of cuts.

SUMMARY OF THE INVENTION

The guide of this invention provides an alternative to a system requiring a plurality of guides or for a guide with a plurality of slots by providing a single guide which slides along the distal femur and which articulates to accommodate a variety of angles. The guide includes a base portion defining a pair of parallel rails having a dove-tail shaped groove formed therein. The base is fixed to the distal end of the femur after an initial cut has been made to flatten the distal end. The device further includes an upper frame which is carried by the base and slides along the rails. The upper frame pivotally supports a carriage assembly in a plurality of discrete angles as determined by detents. The carriage includes a pair of parallel rods which extend in a direction transverse to the parallel rails of the base portion. In the preferred embodiment, the parallel rods support a milling guide which is slidable along the rods. The milling guide is configured to accommodate an elongated milling burr extending therethrough for removal of a portion of the patient's bone.

The sliding arrangement between the base and the upper frame, in combination with the pivotal carriage and sliding milling guide, provide a guide which can direct the milling burr along the bone to form the plurality of surfaces necessary to accommodate the femoral knee implant. Further, with appropriate indicia, the guide can be used to form the necessary surfaces on a wide variety of bones sizes.

Accordingly, it is an object of the invention to provide a novel guide for directing a milling burr or blade along the surface of a bone.

Another object of the invention is to provide a guide having a base portion fixed to the bone and an upper frame portion which is slidable along the base portion.

Another object of the invention is to provide a guide having a carriage assembly that is pivotal relative to an upper frame portion for guiding the milling or cutting devices along the bone in a plurality of angles.

Still other objects of the invention will become apparent upon a reading of the following description taken with the accompanying drawings.

DESCRIPTION OF THE PREFERRED EMBODIMENT

The preferred embodiment herein described is not intended to be exhaustive or limit the application to the precise form disclosed. Rather, it is provided so that others skilled in the art might utilize its teachings.

Figure 1:
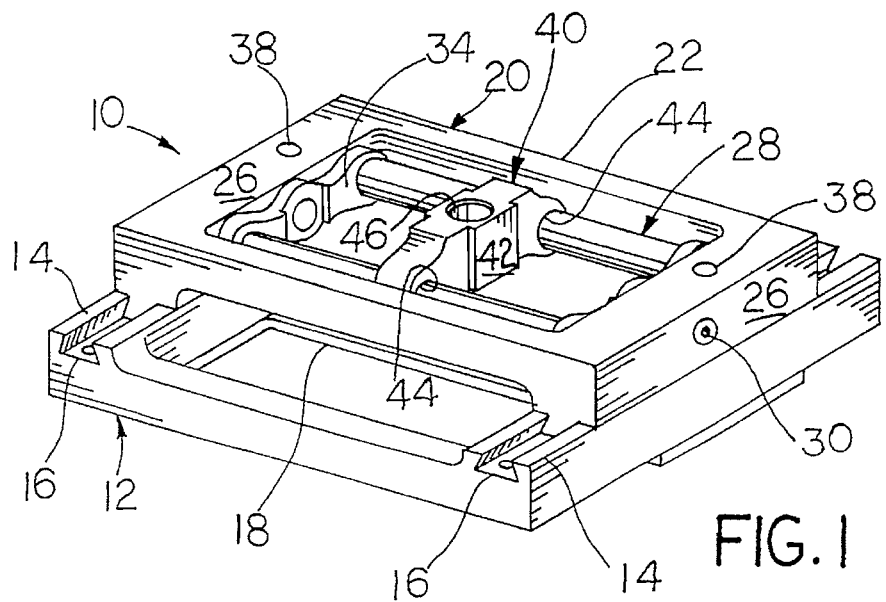
FIG. 1 is a perspective view of the guide of the invention.
Figure 2:
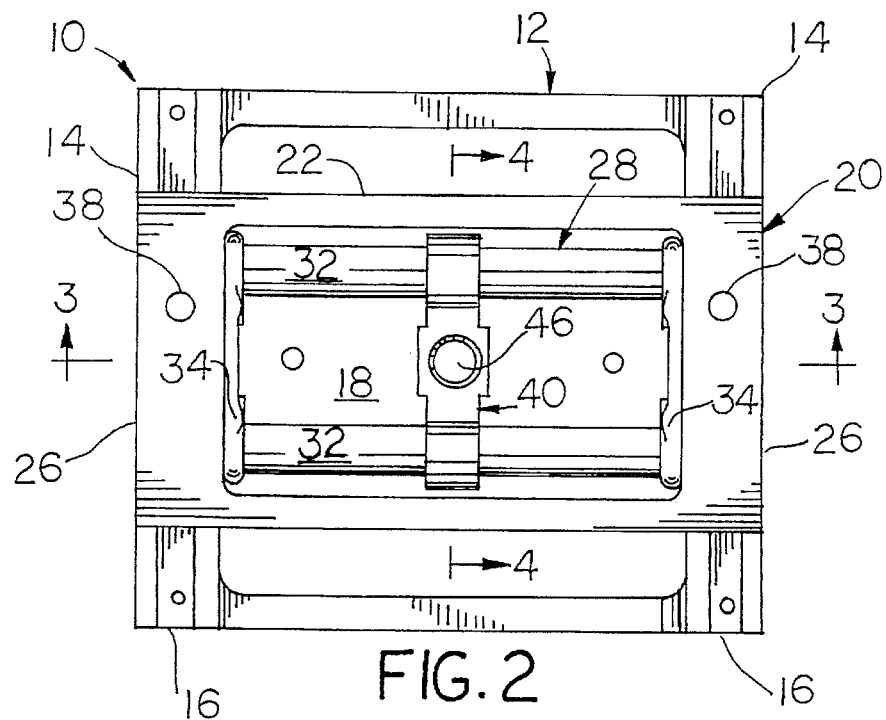
FIG. 2 is a top down elevational view of the guide of the invention.
Figure 3:
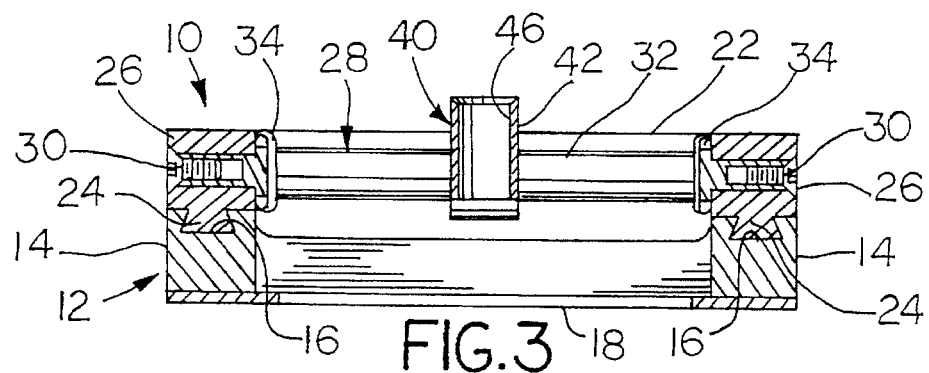
FIG. 3 is a sectional view taken along lines 3—3 of FIG. 2.
Figure 4:
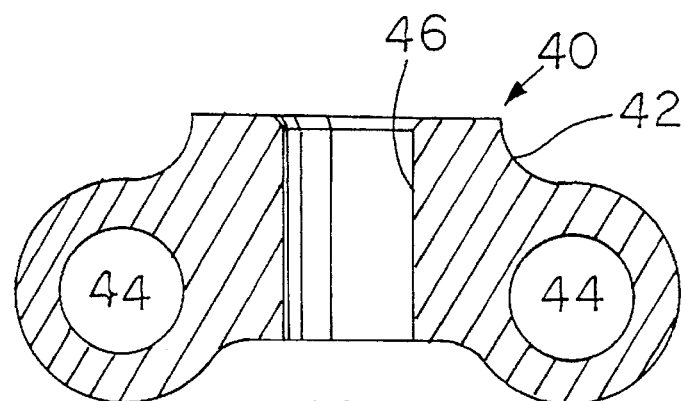
FIG. 4 is an isolated sectional view of the milling guide portion of the invention.
Figure 5:
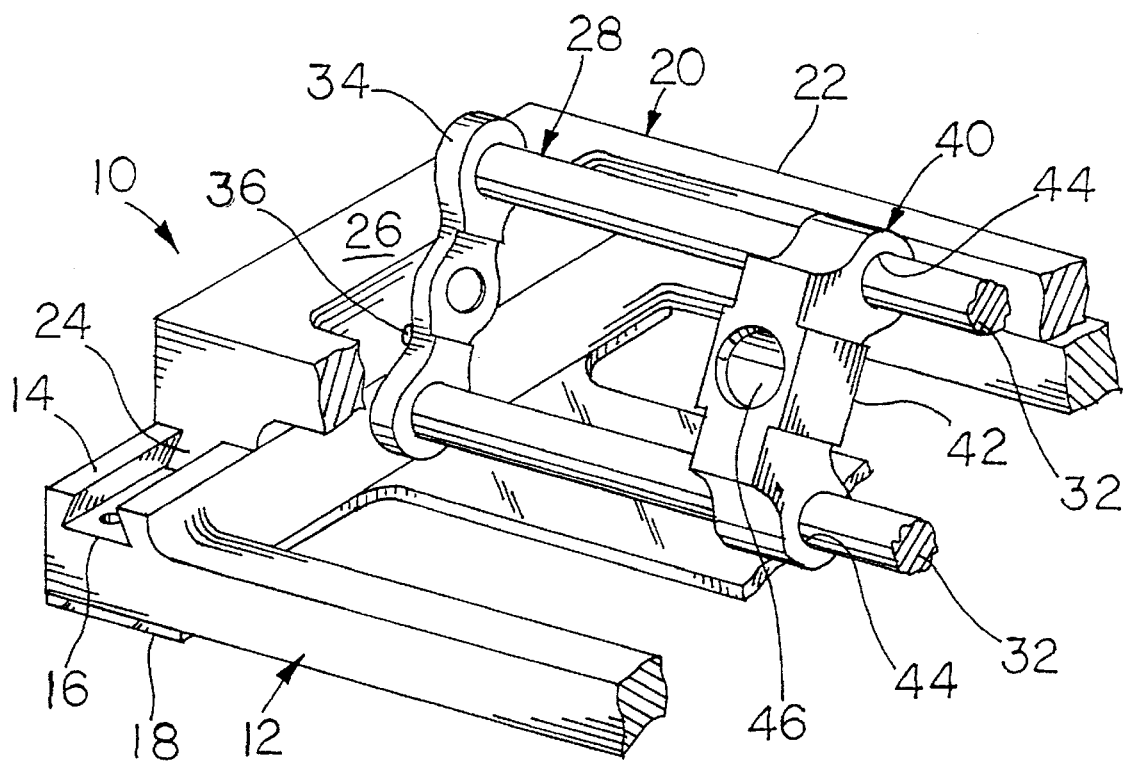
FIG. 5 is a cut-away perspective view of the invention.

The guide 10 includes a generally rectangular base 12 having a pair of parallel sides 14 each having a dove-tail groove 16 formed therein. A foot 18 is connected to base 12 and extends between sides 14. Foot 18 includes a pair of holes therethrough for accommodating a fixation screw (item 19, FIGS. 7–10) therethrough. A slide assembly 20 is carried by base 12. Slide assembly 20 includes a generally rectangular frame 22 having a dove tail shaped rail 24 extending, as illustrated, away from each side 26. Rails 24 are slidably accommodated within the dove tail shaped grooves 16 of sides 14. Slide assembly 20 is shiftable relative to base 12 with rails 24 being captured within the dove tail shaped grooves. Slide assembly 20 further includes an inner frame 28 rotatably carried within the interior of the frame 22 (as illustrated) and connected to frame 22 by a pair of screws 30. Screws 30 together define the axis of rotation of inner frame 28 relative to frame 22. Inner frame 28 includes a pair of parallel rods 32 having a round cross section (see FIG. 5) extending between a pair of end walls 34. A ball detent 36 (FIG. 5) is carried within at least one side 26 to contact an end wall 34 of inner frame 28. A series of recesses (not shown) may be formed within an end wall 34 for engagement with the ball detent 36. A through bore 38 is formed through sides 26 and rails 24 to provide a conduit to introduce a lubricant between the rail and groove. Finally, the rods 32 of inner frame 28 carry a milling guide 40. Milling guide 40 (see FIG. 4) includes a body 42 having a pair of bores 44 extending therethrough for accommodation of rods 32. A transverse through bore 46 is formed through body 42 at a position midway between through bores 44. Milling guide 40 is slidable relative to inner frame 28 along rods 32.

Figure 6:
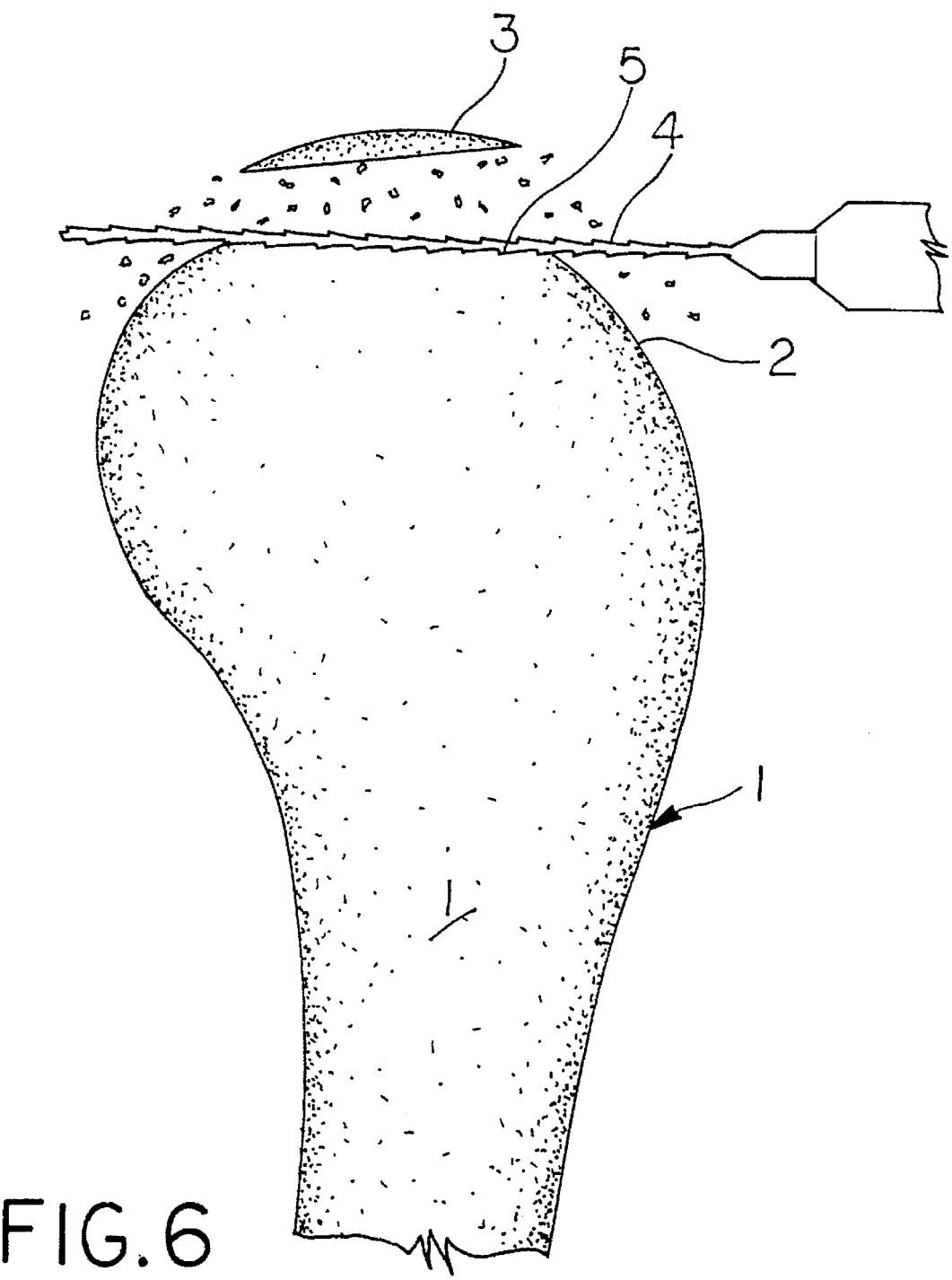
FIG. 6 is an elevational view of a saw blade resetting the distal portion of a femur.
Figure 7:
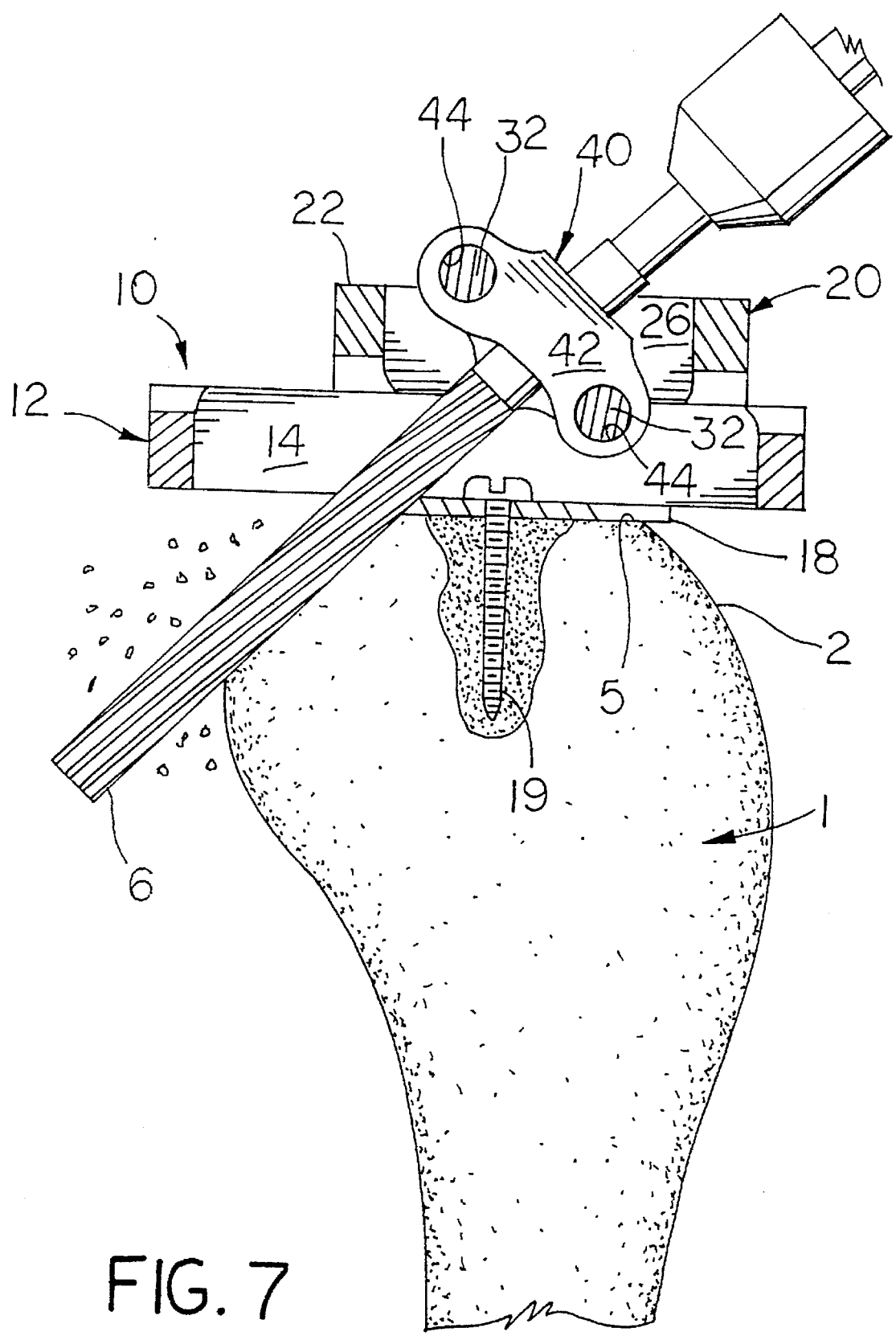
FIG. 7 is a elevational view of the guide of the invention, with portions cut away, connected to the distal end of a femur and guiding a milling device to form a posterior chamfer surface on the bone.

FIGS. 6–10 illustrate the use of guide 10 to mill the distal end 2 of femur 1. Initially, as illustrated in FIG. 6, the surgeon resects the most distal portion 3 of the femur using a conventional saw blade 4. The goal of the resection is to form a flattened distal surface 5 on the femur which defines a reference plane which is perpendicular with anatomical landmarks or reference planes as is well known in the industry. Next, as illustrated in FIG. 7, the surgeon secures the guide 10 to the flattened distal surface 5 by inserting screws 19 through the screw holes in foot 18 of the base 12. With the base secured to the bone, the surgeon rotates inner frame 28 into position to mill the anterior chamfer surface and shifts slide assembly 20 relative to base 12 to remove a predetermined mount of bone. It should be understood that a plurality of measurement indicia and/or stops, not shown, would be provided to guide the surgeon as to the appropriate angles required and distances required so that the resultant surface conforms to the implant. After the guide 40 and inner frame 28 are properly aligned, the surgeon passes a milling burr 6 through bore 46 of guide 40. Preferably, guide 40 is shifted along the inner frame 28 to a position adjacent a side wall 34, and the driver 7, rotating the milling burr, is turned on. With the burr rotating, the surgeon slides the guide along rods 32 toward the opposite side wall 34. In the processes of sliding the guide and burr, the burr is guided across the bone thereby forming a flattened anterior chamfer surface. After the guide contacts the opposite side wall 34, the driver is turned off.

Figure 8:
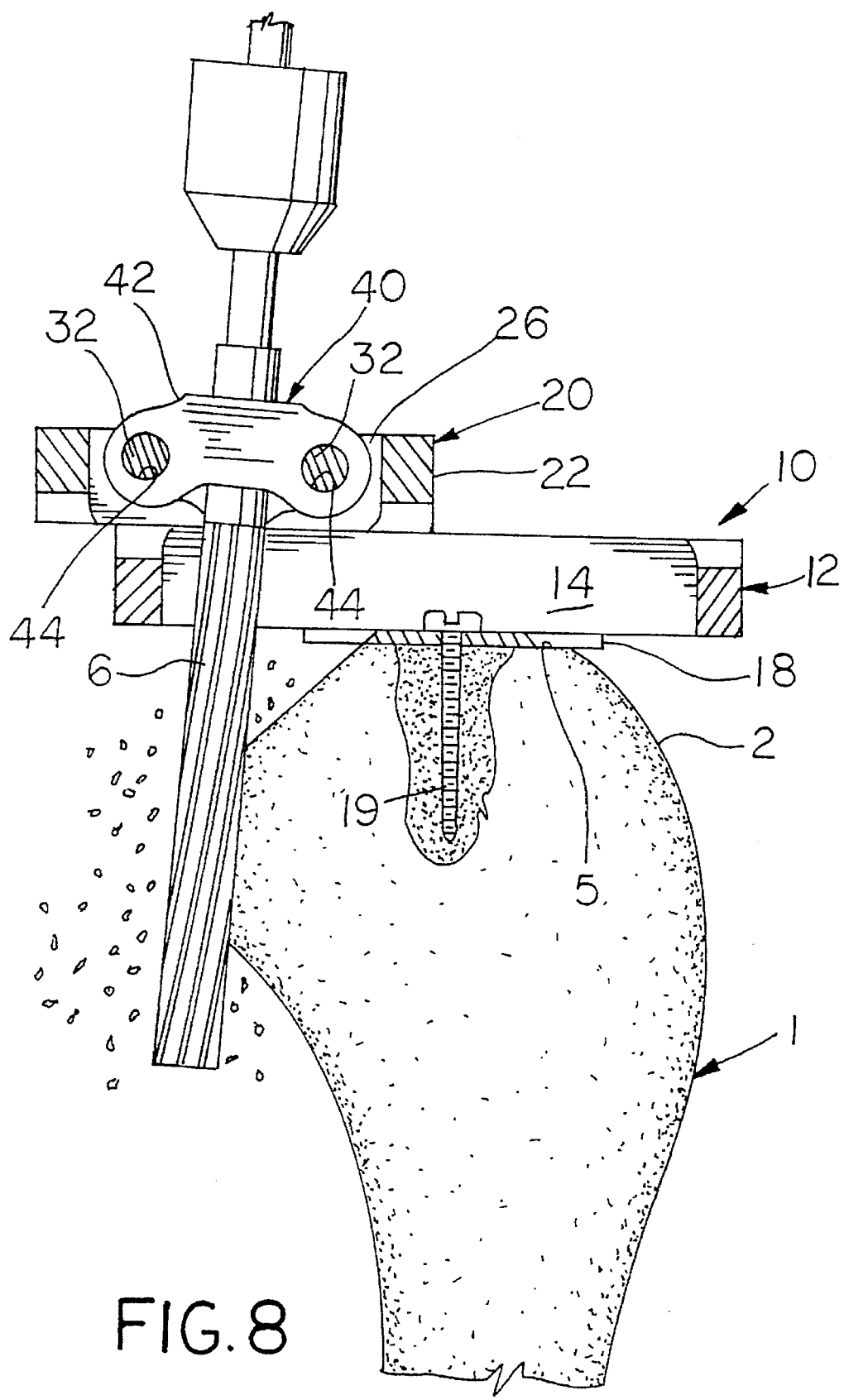
FIG. 8 is the elevational view of FIG. 7 with the guide shifted so as to guide the milling device along the femur to form the posterior surface on the bone.

The surgeon may then shift slide assembly 20 and rotate inner frame 28 into position to form a flattened posterior surface on the femur as illustrated in FIG. 8. The surgeon repeats the process of guiding the burr across the bone by sliding guide 40 along rods 32 from one side wall 34 toward the opposite side wall with the burr rotating.

Figure 9:
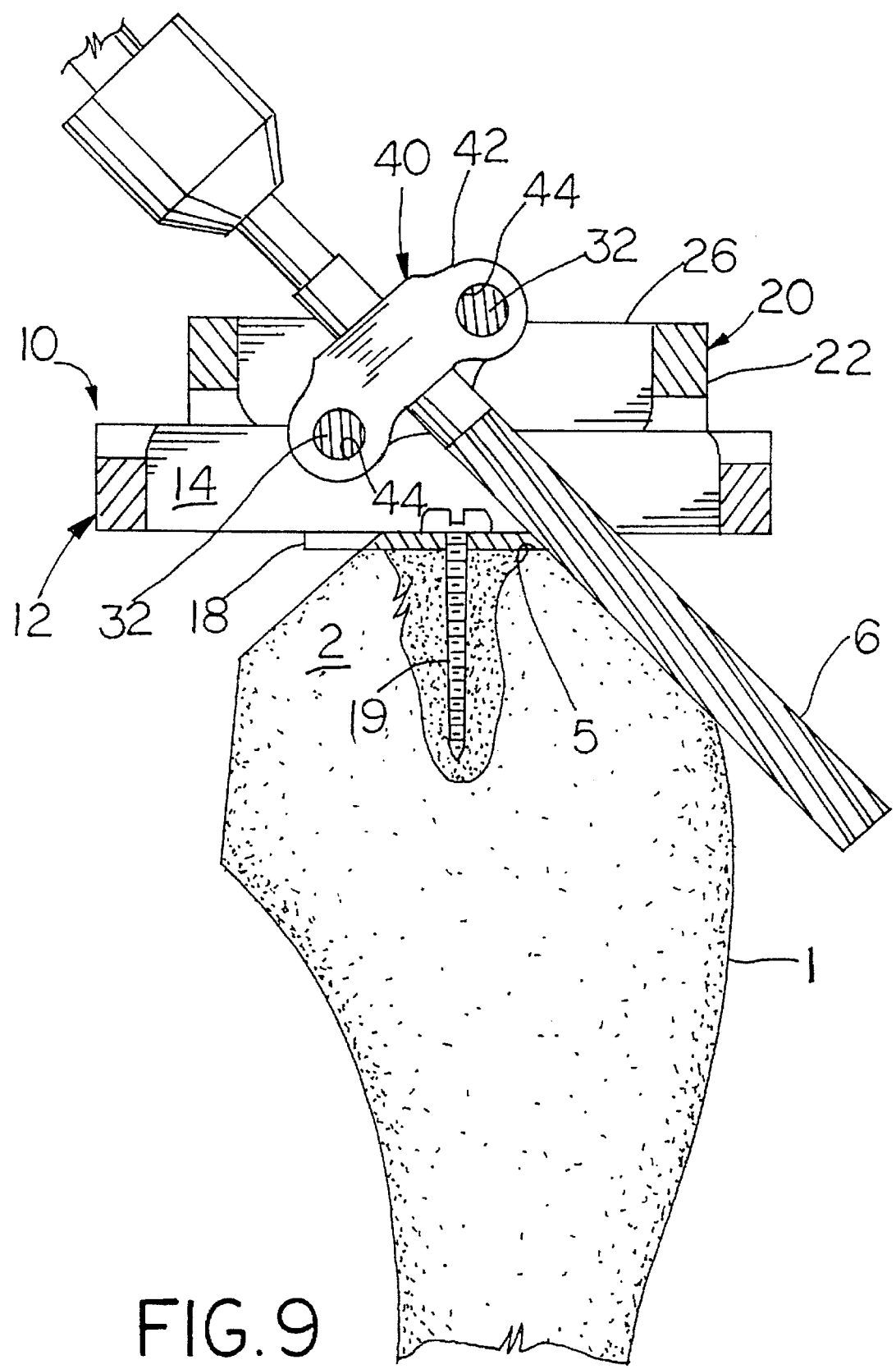
FIG. 9 is the elevational view of FIG. 8 with the guide shifted so as to guide the milling device along the femur to form the anterior chamfer surface on the bone.

Similarly, FIG. 9 illustrates the relative position of guide 40, inner frame 28, and slide assembly 20 relative to base 12 and femur 1 to mill an anterior chamfer surface on the femur. To mill the anterior chaffer surface, the process described above is repeated with the guide 10 in the position illustrated in FIG. 8.

Figure 10:
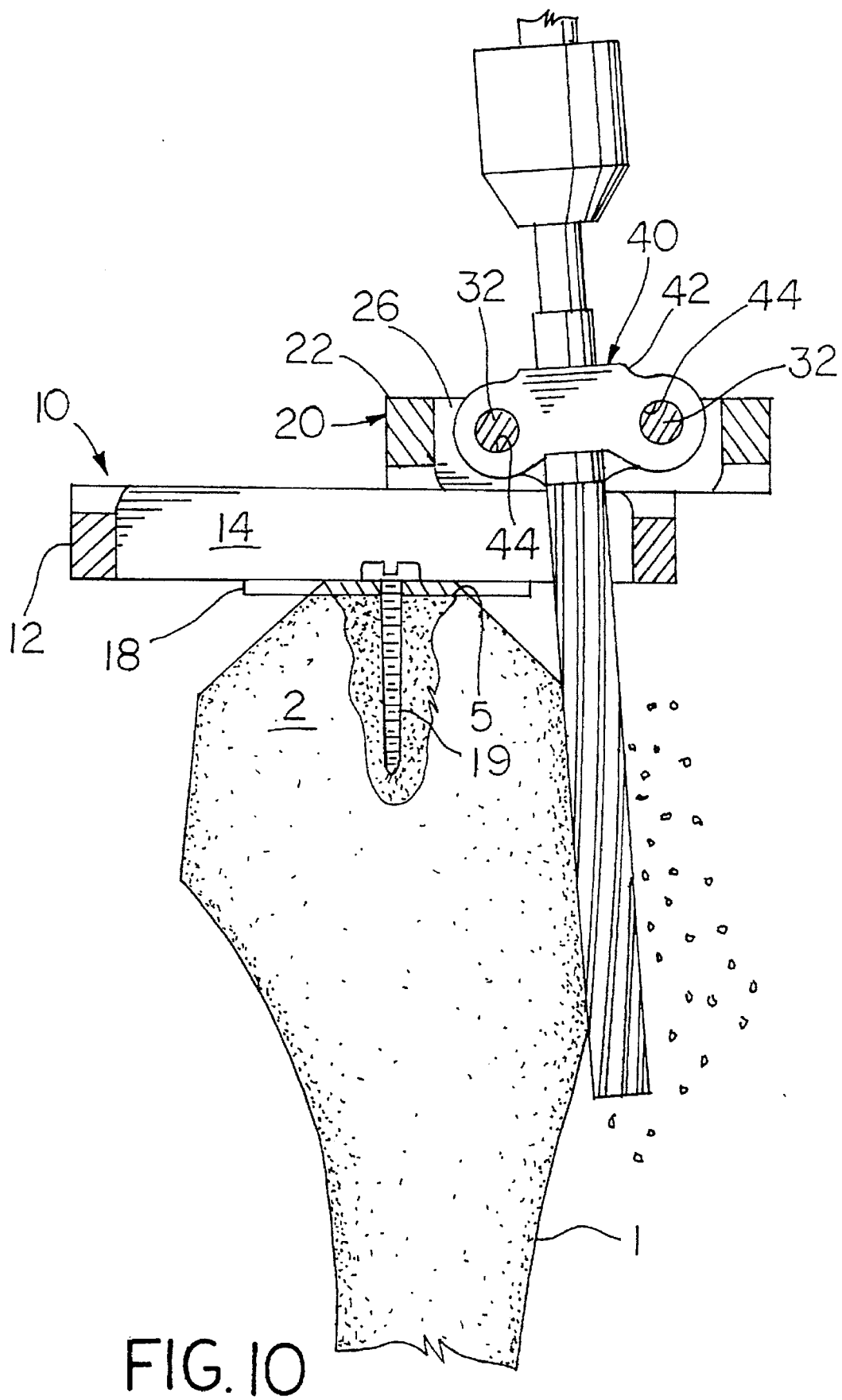
FIG. 10 is the elevational view of FIG. 9 with the guide shifted so as to guide the milling device along the femur to form the anterior surface on the bone.

Finally, FIG. 10 illustrates the relative position of guide 40, inner frame 28, and slide assembly 20 relative to base 12 and femur 1 to mill an anterior surface on the femur. To mill the anterior surface, the process described above is repeated with the guide 10 in the position illustrated in FIG. 8. After milling all of the surfaces necessary, the guide 10 is removed. It should be understood that by utilizing the slide assembly and base of the invention, the guide may accommodate a wide variety of femur/implant sizes with just one guide. With the appropriate indicia and stops on the guide, the surgeon could resect femurs to fit a wide variety of implant sizes and styles while using the same basic technique.

It should also be understood that while the guide has been illustrated and described for use with a willing burr, such should not be considered a limitation on the invention. The guide 40 could easily be modified to accommodate a reciprocating saw blade or any other type of cutting or milling instrument to resect the femur consistent to the manner described above.

Further, it should be understood that while the device has been illustrated in association with a distal femur, the device has applicability to nearly any bone surface requiring multiple resections at intersecting angles.

Finally, it should be understood that the above description has been provided to explain the invention to one skilled in the art. The invention is not to be limited to the details as described above but rather may be modified within the keeping of the appended claims.

We claim:

1. A device for guiding a resection device across a bone to resect a portion of the bone, the device comprising a base, a slide assembly carried by the base and shiftable relative thereto in a first direction, a guide carried by the slide assembly and rotatable relative thereto, said guide configured to accommodate a resection device, said guide being shiftable relative to said slide assembly and base in a second direction, wherein said slide assembly includes a frame which slidably engages the base, an inner frame having a pair of spaced rods supporting said guide, said frame being rotationally connected to the frame so that the side can be rotated relative to said frame, said guide being slidable along said rods relative to said frame.

2. The device of claim 1 wherein said second direction is substantially perpendicular to said first direction.

3. The device of claim 1 wherein said base and frame include cooperating grooves and rails.

4. A device for guiding a resection device along the surface of a bone to shape bone to accommodate a prosthetic implant, the device including a base for contact with said bone and securement thereto, said base being generally rectangular wherein a groove is formed in two opposite side walls, a slide assembly is carried by the base, the slide assembly is substantially rectangular defining an open interior and includes a pair of rails extending from a pair of opposite side walls, the rails being accommodated within the grooves of the base, the slide assembly being shiftable along the grooves of the base, the slide assembly further including an inner frame positioned within the open interior of the slide assembly and being rotatably connected to the slide assembly, the inner frame including a pair of parallel rods and a guide carried by the rods, the guide being configured to accommodate a resection device and is slidable along the rods, wherein the slide assembly slides relative to the base in a first direction and the guide is slidable along the rods in a second direction, the first direction and second direction are substantially perpendicular to one another.

* * * * *